US012766087B2

(12) United States Patent
Prettypaul et al.

(10) Patent No.: US 12,766,087 B2
(45) **Date of Patent: *Oct. 20, 2026**

(54) SUNSCREEN COMPOSITIONS AND METHOD OF USE THEREOF

(71) Applicant: ISP INVESTMENTS LLC, Wilmington, DE (US)

(72) Inventors: Donald I. Prettypaul, Englewood, DE (US); Diane M. Kennedy, Bayonne, NJ (US); Hani M. Fares, Somerset, NJ (US)

(73) Assignee: ISP INVESTMENTS LLC, Wilmington, DE (US)

( * ) Notice: Subject to any disclaimer, the term of this patent is extended or adjusted under 35 U.S.C. 154(b) by 1369 days.

This patent is subject to a terminal disclaimer.

(21) Appl. No.: 17/613,841

(22) PCT Filed: Feb. 18, 2020

(86) PCT No.: PCT/US2020/018539

§ 371 (c)(1),
(2) Date: Nov. 23, 2021

(87) PCT Pub. No.: WO2020/168336

PCT Pub. Date: Aug. 20, 2020

(65) Prior Publication Data

US 2022/0387290 A1 Dec. 8, 2022

Related U.S. Application Data

(60) Provisional application No. 62/806,395, filed on Feb. 15, 2019.

(51) Int. Cl.

| | |
|---|---|
| ***A61K 8/00*** | (2006.01) |
| ***A61K 8/06*** | (2006.01) |
| ***A61K 8/35*** | (2006.01) |
| ***A61K 8/365*** | (2006.01) |
| ***A61K 8/40*** | (2006.01) |
| ***A61K 8/81*** | (2006.01) |
| ***A61Q 17/04*** | (2006.01) |

(52) U.S. Cl.

CPC ............ *A61K 8/8182* (2013.01); *A61K 8/062* (2013.01); *A61K 8/35* (2013.01); *A61K 8/365* (2013.01); *A61K 8/40* (2013.01); *A61Q 17/04* (2013.01)

(58) Field of Classification Search

None

See application file for complete search history.

(56) References Cited

U.S. PATENT DOCUMENTS

| | | | | |
|---|---|---|---|---|
| 2,118,566 | A * | 5/1938 | Miles | A61K 8/24 510/130 |
| 4,842,610 | A | 6/1989 | Gordon et al. | |
| 6,074,652 | A | 6/2000 | Ishiwatari et al. | |
| 6,290,938 | B1 | 9/2001 | Tanner et al. | |
| 6,413,921 | B1 | 7/2002 | Childers et al. | |
| 6,641,821 | B1 | 11/2003 | Collin et al. | |
| 6,685,952 | B1 | 2/2004 | Ma et al. | |
| 7,001,592 | B1 | 2/2006 | Traynor et al. | |
| 7,179,451 | B2 | 2/2007 | Brandt et al. | |
| 7,306,632 | B2 | 12/2007 | Pollack et al. | |
| 7,341,714 | B2 | 3/2008 | Pfaffernoschke et al. | |
| 7,655,305 | B2 | 2/2010 | Rollat et al. | |
| 2005/0008667 | A1 | 1/2005 | Liechty et al. | |
| 2005/0013790 | A1* | 1/2005 | Yamaki | A61Q 19/00 424/74 |
| 2005/0014674 | A1 | 1/2005 | Liechty et al. | |
| 2006/0251602 | A1 | 11/2006 | Goddinger et al. | |
| 2008/0241084 | A1 | 10/2008 | Siddiqui | |
| 2009/0324654 | A1 | 12/2009 | Polonka et al. | |
| 2013/0034514 | A1* | 2/2013 | Schweinsberg | A61K 8/86 556/444 |
| 2014/0140940 | A1* | 5/2014 | Von Thaden | A61K 8/375 424/59 |
| 2014/0142175 | A1 | 5/2014 | Kelada et al. | |
| 2014/0239536 | A1 | 8/2014 | Yoo et al. | |
| 2016/0008244 | A1 | 1/2016 | Castro | |
| 2016/0325010 | A1 | 11/2016 | Liebler et al. | |
| 2017/0333301 | A1 | 11/2017 | Yamaki et al. | |

FOREIGN PATENT DOCUMENTS

| | | | |
|---|---|---|---|
| AU | 0685405 | B2 | 1/1998 |
| EP | 0808624 | A3 | 11/1999 |
| JP | 2011-178710 | A2 | 9/2011 |
| WO | WO2016068300 | A1 | 5/2016 |
| WO | WO2018012557 | A1 | 1/2018 |

OTHER PUBLICATIONS

References cited in the International Search Report of International Application No. PCT/US2020/018539.

* cited by examiner

*Primary Examiner* — Susan T Tran

(74) *Attorney, Agent, or Firm* — Aseem V. Mehta; Nathalie Tietcheu

(57) ABSTRACT

Disclosed herein is a sunscreen composition(s) comprising (i) at least one sunscreen active ingredient(s); (ii) at least one copolymer of vinyl pyrrolidone (VP) and styrene; and (iii) at least one pharmaceutically or cosmetically or dermatologically acceptable excipient. Also disclosed is a method of protecting human skin and animal skin against damages caused by ultra-violet (UV) radiations from the sun rays.

8 Claims, 3 Drawing Sheets

SUNSCREEN COMPOSITIONS AND METHOD OF USE THEREOF

FIELD OF THE PRESENT DISCLOSURE

The presently disclosed process(es), procedure(s), method(s), product(s), composition(s), result(s) and/or concept(s) (collectively referred to hereinafter as the "present disclosure") relates to sunscreen composition(s) with enhanced Sun Protection Factor (SPF) value. The present disclosure further relates to a method(s) of use of such compositions.

BACKGROUND OF THE PRESENT DISCLOSURE

Sunscreen products are used to protect skin against the harmful effects of solar radiations, particularly Ultraviolet (UV) radiations. Prolonged exposure to UV radiation is a proven cause for severe skin ailments such as skin cancer, skin aging and sun burn. UV radiation is the broad-spectrum radiation subdivided into UVC (100-290 nm), UVB (290-320 nm) and UVA (320-400 nm) regions. UVC radiation is filtered off the from the atmosphere along with partly UVB radiation, however most of the remaining UVB radiation together with UVA radiation reach skin and causes biological and metabolic reactions. UVA radiation penetrates deep into the skin (dermis) and mainly responsible for genetic (DNA) damage to cells, inflammation, photo-ageing (wrinkling, blotchiness) and immune-suppression. Whereas, UVB radiation penetrates into the epidermis (top layer of the skin) and mainly causes suntan, sunburn and in severe cases, blistering. Both the VU radiations are associated with skin cancer. Sunscreens products are cosmetic preparations containing sunscreen filters that absorb, reflect or scatter the harmful solar radiation. Majority of the sunscreen filters used in the sunscreen products provide protection against the harmful effects of UVB and UVA radiations. The Sun Protection Factor (SPF) parameter is used to quantify the effectiveness of a sunscreen product. The SPF value is measured as the ratio of the irradiation time required to attain the erythema-forming threshold with the UV filter present to the time required to attain the same threshold in the absence of the UV filter.

Therefore, sunscreen products with high SPF value are always in great demand. However, among UVA and UVB sunscreen filters, only UVB filters contribute to the SPF value of a sunscreen product. Thus, high SPF values ordinarily are obtained by incorporating a large amount of UVB absorbing sunscreen filters. However, the addition of UVB filters in large quantities can lead to undesirable effects such as high viscosity, skin irritancy as well as increased cost of products. Further, the sunscreen filter should also effectively block both UVB and UVA rays, which is possible with a sunscreen filter having an SPF of 30 or greater. Other approaches include using small amounts of UV absorbers like butyl salicylate or by adding light scattering/refracting polymers such as styrene/acrylate copolymer.

U.S. Pat. No. 6,641,821 discloses a cosmetic or dermatological film-forming composition comprising a liquid fatty phase, including at least one volatile hydrocarbon oil, and a film-forming polymer in said liquid fatty phase, characterized in that it comprises at least one polyolefin wax resulting from the polymerization of alpha-olefins having at least 10 carbon atoms, said wax having a melting point ranging from 50 to 80° C. The invention includes the use of such a composition, especially for producing a water-resistant film exhibiting good hold with regard to rubbing, to tears, to perspiration or to sebum.

U.S. Pat. No. 7,001,592 B1 discloses about an invention that encompasses additives for addition to a bodywash, where the additives contain one or more sunscreens, and where a bodywash which contains the additive imparts to the skin an SPF of at least about 2, in some cases at least about 5, or 10, or 15. Also described are methods of making and using the additives.

U.S. Pat. No. 6,685,952 B1 discloses a composition which is: (A) A hair care composition which is a high internal phase water-in-oil emulsion which comprises: (I) an oil phase which further comprises (i) a mixture of non-volatile and volatile silicone oils, and (ii) a silicone surfactant; and (II) which comprises an aqueous phase; and which substantially lacks a fatty alcohol; and (B) A skin care composition which is a high internal phase water-in-oil emulsion which comprises: (I) an oil phase which further comprises (i) a mixture of non-volatile and volatile silicone oils, and (ii) a silicone surfactant; and (III) which comprises an aqueous phase.

US Patent Publication No. 2005014674 A1 discloses a cosmetic composition for caring for and/or making up the skin and/or the lips, comprising at least one liquid fatty phase, the said fatty phase containing at least one lipodispersible film-forming polymer and polyethylene particles with a number-average size of less than or equal to 50 mum.

US Patent Publication No. 2005008667 A1 discloses a cosmetic composition for caring for and/or making up the skin and/or the lips, comprising at least one liquid fatty phase, the said fatty phase containing at least one film-forming polymer and silicate particles.

In view of the foregoing, there remains a long felt need for a sunscreen composition(s) with enhanced SPF value wherein the enhanced SPF value is particularly achieved by without increasing the amount of sunscreen active ingredients.

SUMMARY OF THE PRESENT DISCLOSURE

In one aspect, the present disclosure provides a sunscreen composition comprising: (i) 0.01 wt. % to 20 wt. % of (a) a first copolymer of vinyl pyrrolidone (VP) and styrene, and (b) optionally a second copolymer of vinyl pyrrolidone (VP) and at least one $C_2$ to $C_{40}$ alkene; (ii) 0.01 wt. % to 50 wt. % of at least one sunscreen active ingredient(s); and (iii) 0.01 wt. % to 50 wt. % of at least one pharmaceutically or cosmetically or dermatologically acceptable excipient.

In one embodiment of the present disclosure, the $C_2$ to $C_{40}$ alkene comprises $C_2$ to $C_{40}$ aliphatic alkene or $C_2$ to Cao aromatic alkene or any combinations thereof. Further, the $C_2$ to $C_{40}$ aliphatic alkene can be a linear or a branched chain alkene selected from the group consisting of pentadecene, hexadecene, heptadecene, octadecene, nonadecene, eicosene, docosene, triacontene, and any combinations thereof. In another embodiment of the present disclosure the second copolymer is (i) a vinyl pyrrolidone (VP)/eicosene copolymer or (ii) a vinyl pyrrolidone (VP)/hexadecene copolymer or (iii) a vinyl pyrrolidone (VP)/triacontene copolymer or any combinations thereof. In still another embodiment, the sunscreen composition comprises a mixture of (a) vinyl pyrrolidone (VP)/styrene copolymer as the first copolymer and (b) vinyl pyrrolidone (VP)/eicosene copolymer as the second copolymer.

In another aspect, the present disclosure provides a sunscreen composition comprising: (i) 0.01 wt. % to 20 wt. % of vinyl pyrrolidone (VP)/styrene copolymer; (ii) 0.01 wt. % to 50 wt. % of at least one sunscreen active ingredient selected from the group consisting of butyl methoxydibenzoylmethane, octyl salicylate, octocrylene, benzophenone-3 and homosalate; and (iii) 0.01 wt. % to 50 wt. % of at least one pharmaceutically or cosmetically or dermatologically acceptable excipient. In one embodiment of the present disclosure, the sunscreen composition further comprises a vinyl pyrrolidone (VP)/eicosene copolymer.

In still another aspect, the present disclosure provides a method of protecting human skin and animal skin against damages caused by ultra-violet (UV) radiations, comprising applying the sunscreen composition of the present disclosure to the human skin and animal skin.

In yet another aspect, the present disclosure provides a use of a sunscreen composition for protecting human skin and animal skin against damages caused by ultra-violet (UV) radiations, wherein the composition comprising: (i) 0.01 wt. % to 20 wt. % of (a) a first copolymer of vinyl pyrrolidone (VP) and styrene, and (b) optionally a second copolymer of vinylpyrrolidone (VP) and at least one $C_2$ to $C_{40}$ alkene; (ii) 0.01 wt. % to 50 wt. % of at least one sunscreen active ingredient(s); and (iii) 0.01 wt. % to 50 wt. % of at least one pharmaceutically or cosmetically or dermatologically acceptable excipient.

BRIEF DESCRIPTION OF THE PRESENT FIGURES

Objects, features, and advantages of the present invention will become apparent upon reading the following description in conjunction with the drawings/figures, in which.

DETAILED DESCRIPTION OF THE PRESENT DISCLOSURE

Figure 1:
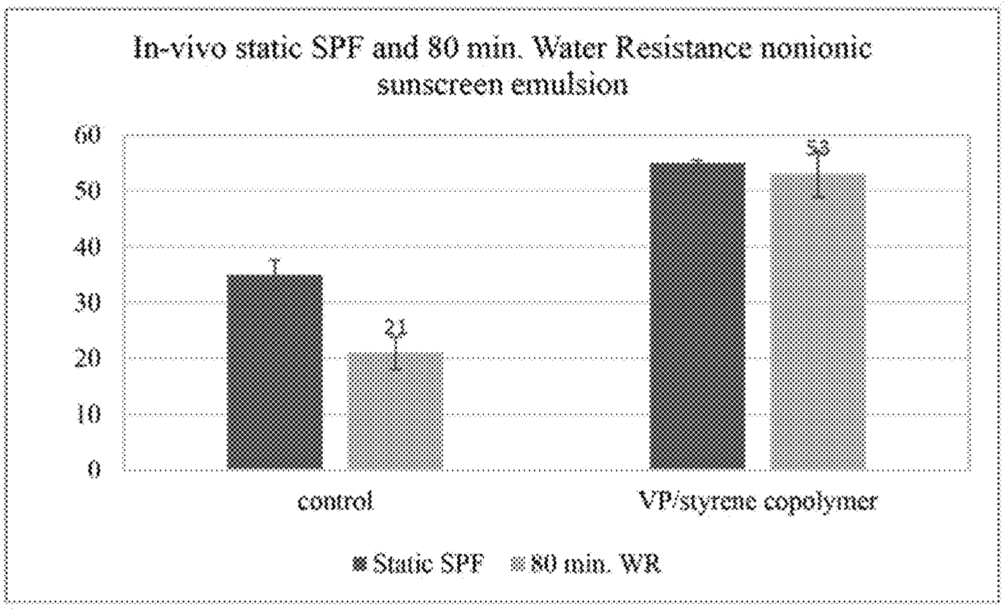
FIG. 1 shows "in-vivo" SPF testing results of sunscreen composition (non-ionic emulsion) comprising VP/styrene copolymer.

Before explaining at least one embodiment of the present disclosure in detail, it is to be understood that the present disclosure is not limited in its application to the details of construction and the arrangement of the components or steps or methodologies set forth in the following description or illustrated in the drawings. The present disclosure is capable of other embodiments or of being practiced or carried out in various ways. Also, it is to be understood that the phraseology and terminology employed herein is for the purpose of description and should not be regarded as limiting.

Unless otherwise defined herein, technical terms used in connection with the present disclosure shall have the meanings that are commonly understood by those of ordinary skill in the art. Further, unless otherwise required by context, singular terms shall include pluralities and plural terms shall include the singular.

All patents, published patent applications, and non-patent publications mentioned in the specification are indicative of the level of skill of those skilled in the art to which the present disclosure pertains. All patents, published patent applications, and non-patent publications referenced in any portion of this application are herein expressly incorporated by reference in their entirety to the same extent as if each individual patent or publication was specifically and individually indicated to be incorporated by reference.

As utilized in accordance with the present disclosure, the following terms, unless otherwise indicated, shall be understood to have the following meanings.

The use of the word "a" or "an" when used in conjunction with the term "comprising" may mean "one," but it is also consistent with the meaning of "one or more, at least one," and "one or more than one." The use of the term "or" is used to mean "and/or" unless explicitly indicated to refer to alternatives only if the alternatives are mutually exclusive, although the disclosure supports a definition that refers to only alternatives and "and/or." Throughout this application, the term "about" is used to indicate that a value includes the inherent variation of error for the quantifying device, the method being employed to determine the value, or the variation that exists among the study subjects. For example, but not by way of limitation, when the term "about" is utilized, the designated value may vary by plus or minus twelve percent, or eleven percent, or ten percent, or nine percent, or eight percent, or seven percent, or six percent, or five percent, or four percent, or three percent, or two percent, or one percent. The use of the term "at least one" will be understood to include one as well as any quantity more than one, including but not limited to, 1, 2, 3, 4, 5, 10, 15, 20, 30, 40, 50, 100, etc. The term "at least one" may extend up to 100 or 1000 or more depending on the term to which it is attached. In addition, the quantities of 100/1000 are not to be considered limiting as lower or higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first", "second", "third", "fourth", etc.) is solely for the purpose of differentiating between two or more items and, unless otherwise stated, is not meant to imply any sequence or order or importance to one item over another or any order of addition.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. The term "or combinations thereof" as used herein refers to all permutations and combinations of the listed items preceding the term. For example, "A, B, C, or combinations thereof" is intended to include at least one of: A, B, C, AB, AC, BC, or ABC and, if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context. As used herein, the term "polymer" refers to a large molecule comprising one or more types of monomer residues (repeating units) connected by covalent chemical bonds. By this definition, polymer encompasses compounds wherein the number of monomer units may range from very few, which more commonly may be called as oligomers, to very many. Non-limiting examples of polymers include homopolymers, and non-homopolymers such as copolymers, terpolymers, tetrapolymers and the higher analogues. The polymer may have a random, block, and/or alternating architecture.

As used herein, the term "copolymer" refers to a non-homopolymer that comprises two or more different monomer types.

As used herein, the term "sun care composition" or "sunscreen composition" refers to a composition intended for use on human body (human skin) and/or animal body (animal skin) for protection from harmful or undesirable radiations from the sun.

As used herein, the term "UVA" refers to ultraviolet electromagnetic radiations with a wavelength of from about 320 nm to about 400 nm and includes UV-A1 (from about 340 nm to about 400 nm) and UV-A2 (from about 320 nm to about 340 nm).

As used herein, the term "UVB" refers to ultraviolet electromagnetic radiation with a wavelength of from about 290 nm to about 320 nm.

As used herein, the term "sunscreen" refers to personal care, sun care and/or pharmaceutical composition comprising an effective amount of one or more sunscreen active ingredient(s). Sunscreen composition can include bleach and non-bleach products that are applied to the face, decollete, lips and skin to treat and/or protect against erythema, burns, wrinkles, lentigo ("liver spots"), skin cancers, keratotic lesions, and cellular changes of the skin. Other categories of sunscreens that fit into this definition are sun blocks, all-day protection formulas, baby sun care and tanning preparations that have UV absorber(s).

As used herein, the term, "emulsifier" refers to a compound/composition that aids in the formation of an oil in water, or a water in oil emulsion.

As used herein, the term "alkene" refers to a hydrocarbon olefin that has at least one non-aromatic carbon-carbon double bond. The term "alkene" includes aliphatic or aromatic (an alkene having an aromatic substituent within the compound), cyclic or acyclic, and/or linear and branched compounds having at least one non-aromatic carbon-carbon double bond unless expressly stated otherwise. Alkenes having only one, only two, only three, and so forth, carbon double bonds can be identified by use of the term "mono," "di," "tri," and so forth, within the name. For example, alkamonoenes, alkadienes, and alkatrienes refer to a linear or branched hydrocarbon olefins having only one carbon-carbon double bond (general formula $C_nH_{2n}$), only two carbon-carbon double bonds (general formula $C_nH_{2n-2}$), and only three carbon-carbon double bonds (general formula $C_nH_{2n-4}$), respectively. Alkenes can be further identified by the position of the carbon-carbon double bond(s). Other identifiers can be utilized to indicate the presence or absence of particular groups within an alkene. For example, a haloalkene refers to an alkene having one or more hydrogen atoms replace with a halogen atom.

As used herein, the term "pharmaceutically or cosmetically or dermatologically acceptable excipients" means an ingredient or a combination of the ingredients that can be used in the sunscreen composition of the present disclosure. The excipient can be selected from the group consisting of skin-feel additives, moisturizing agents, film forming agents, waterproofing agents, pH adjusters, chelating agents, anti-aging agents, exfoliating agents, fragrances, emulsifiers, surfactants, rheology modifiers, preservatives, emollients, waxes, conditioners, lubricants, anti-oxidants, diluents, co-solvents, humectants, and any combinations thereof.

In one aspect, the present disclosure provides a sunscreen composition comprising: (i) 0.01 wt. % to 20 wt. % of (a) a first copolymer of vinyl pyrrolidone (VP) and styrene, and (b) optionally a second copolymer of vinyl pyrrolidone (VP) and at least one $C_2$ to $C_{40}$ alkene; (ii) 0.01 wt. % to 50 wt. % of at least one sunscreen active ingredient(s); and (iii) 0.01 wt. % to 50 wt. % of at least one pharmaceutically or cosmetically or dermatologically acceptable excipient. A suitable vinyl pyrrolidone (VP) and styrene copolymer is Polectron™ 430 (Ashland).

In one embodiment of the present disclosure, the sunscreen composition can only comprise the copolymer of vinyl pyrrolidone (VP) and styrene as the first copolymer. Alternatively, the sunscreen composition of the present disclosure can also comprise a mixture of the first copolymer and the second copolymer, wherein the first copolymer can include the copolymer of VP and styrene, and the second copolymer can include at least one copolymer of VP and at least one $C_2$ to $C_{40}$ alkene.

The $C_2$ to $C_{40}$ alkene used in the second copolymer of the present disclosure can include $C_2$ to $C_{40}$ aliphatic alkenes or $C_2$ to $C_{40}$ aromatic alkenes (aryl substitute alkene) or any combinations thereof. In one embodiment of the present disclosure, the $C_2$ to $C_{40}$ alkene can include $C_2$ to $C_{40}$ aliphatic alkene. Further, the $C_2$ to $C_{40}$ aliphatic alkene can be a linear alkene or a branched chain alkene. Examples of such alkenes can include, but are not limited to, pentadecene, hexadecene, heptadecene, octadecene, nonadecene, eicosene, docosene and triacontene.

Further, the second copolymer of VP and $C_2$ to $C_{40}$ alkene can be a single copolymer. Alternatively, the second copolymer can be a mixture of two or more second copolymers. Suitable examples of the second copolymer can include, but are not limited to, vinyl pyrrolidone (VP)/eicosene copolymer, vinyl pyrrolidone (VP)/hexadecene copolymer or vinyl pyrrolidone/triacontane copolymer.

In one non-limiting embodiment of the present disclosure, the sunscreen composition comprises a mixture of (a) VP/styrene copolymer as the first copolymer and (b) VP/eicosene copolymer as the second copolymer, and wherein the VP/styrene copolymer and VP/eicosene copolymer can be mixed together in a weight ratio of from 2 to 10:1 to 4.

In another embodiment of the present disclosure, the amount of the first copolymer either alone or in combination with the second copolymer can vary in the range of from about 0.1 wt. % to about 10.0 wt. % of the total composition weight. Other non-limiting % ranges of the copolymers employed in the sunscreen composition of the present disclosure includes from about 1.0 wt. % to about 10.0 wt. %; from about 1.0 wt. % to about 8.0 wt. %; from about 2.0 wt. % to about 8.0 wt. %; from about 3.0 wt. % to about 8.0 wt. %; from about 4.0 wt. % to about 7.0 wt. %; from about 5.0 wt. % to about 6.0 wt. %; from about 6.0 wt. % to about 7.0 wt. %; from about 7.0 wt. % to about 8.0 wt. %; from about 8.0 wt. % to about 9.0 wt. %; or from about 9.0 wt. % to about 10.0 wt. % of the total composition weight.

The sunscreen composition of present disclosure can further comprise one or more sunscreen active ingredients. These ingredients can be selected from the group consisting of UVA sunscreen filters, UVB sunscreen filters, physical sun blockers, or any combinations thereof. Examples of the UVA and/or UVB sunscreen filters can include, but are not limited to, butyl methoxydibenzoylmethane (Avobenzone); octyl salicylate (ethyl hexyl salicylate); pentyl dimethyl PABA; octyl dimethyl PABA; benzophenone-1; benzophenone-6; 2-(2H-benzotriazol-2-yl)-4,6-di-tert-pentylphenol; ethyl-2-cyano-3,3-diphenylacrylate; homomethyl salicylate (homosalate); bis-ethylhexyloxyphenol methoxyphenyl triazine; methyl-(1,2,2,6,6-pentamethyl-4-piperidyl)-sebacate; 2-(2H-benzotriazol-2-yl)-4-methylphenol; diethylhexyl butamido triazone; amyl dimethyl PABA; 4,6-bis(octylthiomethyl)-o-cresol; red petroleum; ethylhexyl triazone; octocrylene; isoamyl-p-methoxycinnamate; drometrizole; titanium dioxide; 2,4-di-tert-butyl-6-(5-chloro-2H-benzotriazole-2-yl)-phenol; 2-hydroxy-4-octyloxybenzophenone; benzophenone-2; diisopropyl methylcinnamate; PEG-25 PABA; 2-(1,1-dimethylethyl)-6-[[3-(1,1-demethylethyl)-2-hydroxy-5-methylphenyl] methyl-4-methylphenyl acrylate; drometrizole trisiloxane; menthyl anthranilate; butyl methoxydibenzoylmethane; 2-ethoxyethyl p-methoxycinnamate; benzylidene camphor sulfonic acid; dimethoxyphenyl-[1-(3,4)]-4,4-dimethyl 1,3-pentanedione; zinc oxide; N,N'-hexane-1,6-diylbis[3-(3,5-di-tert-butyl-4-hydroxyphenylpropionamide)]; pentaerythritol tetrakis[3-(3,5-di-tert-butyl-4-hydroxyphenyl) propionate]; 2,6-di-tert-butyl-4-[4,6-bis(octylthio)-1,3,5-triazin-2-ylamino]phenol; 2-(2H-benzotriazole-2-yl)-4,6-bis (1-methyl-1-phenylethyl)phenol; trolamine salicylate; diethylanolamine p-methoxycinnamate; polysilicone-15; 4-methylbenzylidene camphor; bisoctrizole; N-phenyl-benzenamine; reaction products with 2,4,4-trimethylpentene; sulisobenzone; (2-ethylhexyl)-2-cyano-3,3-diphenylacrylate; digalloyl trioleate; polyacrylamido methylbenzylidene camphor; glyceryl ethylhexanoate dimethoxycinnamate; 1,3-bis-[(2'-cyano-3',3'-diphenylacryloyl)oxy]-2,2-bis-[(2'-cyano-bis-(2,2,6,6-tetramethyl-4-piperidyl)-sebacate; benzophenone-5; 1,3,5-tris(3,5-di-tert-butyl-4-hydroxybenzyl)-1,3,5-triazine-2,4,6(1H,3H,5H)-trione; hexamethylendiamine; benzophenone-8; ethyl-4-bis(hydroxypropyl)aminobenzoate; 6-tert-butyl-2-(5-chloro-2H-benzotriazole-2-yl)-4-methylphenol; p-aminobenzoic acid; 3,3',3",5,5',5"-hexa-tert-butyl-a-a'-a"-(mesitylene-2,4,6-triyl)tri-p-cresol; lawsone with dihydroxyacetone; benzophenone-9; benzophenone-4; ethylhexyl dimethoxy benzylidene dioxoimidazoline propionate; N,N'-bisformyl-N,N'-bis-(2,2,6,6-tetramethyl-4-piperidinyl); 3-benzylidene camphor; terephthalylidene dicamphor sulfonic acid; camphor benzalkonium methosulfate; bisdisulizole disodium; etocrylene; ferulic acid; 2-(2H-benzotriazole-2-yl)-4-(1,1,3,3-tetramethylbutyl)-phenol; 4,6-bis(dodecylthiomethyl)-o-cresol; β-2-glucopyranoxy propyl hydroxy benzophenone; phenylbenzimidazole sulfonic acid; benzophenone-3; diethyl amino hydroxybenzoyl hexylbenzoate; 3',3'-diphenylacryloyl)oxy]methyl}-propane; ethylhexyl p-methoxycinnamate, and any combinations thereof.

Similarly, suitable examples of the physical sun blockers can include, but are not limited to, cerium oxides, chromium oxides, cobalt oxides, iron oxides, red petrolatum, silicone-treated titanium dioxides, titanium dioxides, zinc oxides and/or zirconium oxides, and mixtures thereof. The sunscreen active ingredients can be present in an amount of from about 0.01 wt. % to about 50 wt. % of the total composition weight. Other non-limiting wt. % of the sunscreen active ingredients can vary in the range of from about 0.1 wt. % to about 10.0 wt. % or from about 1.0 wt. % to about 5.0 wt. % of the total composition weight.

The sunscreen composition of the present disclosure can further comprise at least one pharmaceutically or cosmetically or dermatologically acceptable excipient. These excipients can include, but are not limited to, skin-feel additives, moisturizing agents, film forming agents, waterproofing agents, pH adjusters, chelating agents, anti-aging agents, exfoliating agents, fragrances, emulsifiers, surfactants, rheology modifiers, preservatives, emollients, waxes, conditioners, lubricants, anti-oxidants, diluents, co-solvents, humectants, and combinations thereof. These excipients can be present in an amount of from about 0.01 wt. % to about 50.0 wt. % or from about 0.01 wt. % to about 10.0 wt. % or from about 10 wt. % to about 25.0 wt. % or from about 25.0 wt. % to about 50.0 wt. % of the total composition weight.

Examples of suitable emulsifiers can include, but are not limited to, glycol distearate, sorbitan trioleate, glycol stearate, sorbitan sesquioleate, glyceryl stearate, glyceryl dilaurate, lecithin, sorbitan oleate, sorbitan stearate, sorbitan isostearate, oleth-2 and steareth-2, calcium stearoyl lactylate, glyceryl laurate, ceteth-2, PEG-30 dipolyhydroxystearate, glyceryl stearate SE, PEG-4 dilaurate, sorbitan stearate (and) sucrose cocoate, methyl glucose sesquistearate, sucrose stearate, PEG-10 sunflower glycerides, sodium stearoyl lactylate, sorbitan laurate, PEG-40 sorbitan peroleate, lecithin, laureth-4, PEG-7 glyceryl cocoate, PEG-20 almond glycerides, linoleamide DEA, PEG-25 hydrogenated castor oil, cetearyl glucoside, polysorbate 85, glyceryl stearate (and) PEG-100 stearate, stearamide MEA, oleth-10/polyoxyl 10 oleyl ether NF, oleth-10, oleth-20, ceteth-10, PEG-8 laurate, cocamide MEA, polysorbate 60, PEG-60 almond glycerides, isosteareth-20, lauramide DEA, PEG-30 dipolyhydroxystearate, polysorbate 80, PEG-20 methyl glucose sesquistearate, ceteareth-20, oleth-20, steareth-21, ceteth-20, isoceteth-20, polysorbate 20, laureth-23, PEG-100 stearate, PEG-80 sorbitan laurate, potassium cetyl phosphate, cetearyl alcohol, diacetyl phosphate, ceteth-10 phosphate, and any combinations thereof.

Similarly, suitable examples of the co-solvent(s) can include, but are not limited to, one or more polyols, esters, ethers, propoxylated esters, propoxylated alcohols, and alkoxylated alcohols, and any combinations thereof.

Examples of preservatives or preservative systems that can be used in the sunscreen composition of the present disclosure can include, but are not limited, lower alkyl esters of para-hydroxybenzoates (parabens) such as methylparaben, ethylparaben, propylparaben and isobutylparaben; benzyl alcohol; phenoxyethanol; benzoic acid, and combinations thereof.

Further, in one embodiment of the present disclosure, the first copolymer either alone or when present in combination with the second copolymer can also act as a film forming agent. In this embodiment, the sunscreen composition of the present disclosure may not comprise any additional film forming agents. Alternatively, the sunscreen composition of the present disclosure can further optionally comprise at least one additional film forming agent. Suitable examples of such additional film forming agents can include, but are not limited to, Acrylates/$C_{12}$-$C_{22}$ Alkyl Methacrylate Copolymer (Allianz OPT available from Ashland LLC), acrylate copolymers, octyldodecyl citrate copolymer, VP/acrylate/lauryl methacrylate copolymer, acrylic acid/VO cross copolymer, and any combinations thereof.

Additional thickening or viscosity increasing agents can also be added in the present sunscreen composition. Examples of such additional thickening or viscosity increasing agents can include, but are not limited to, acetamide MEA; acrylamide/ethalkonium chloride acrylate copolymer; acrylamide/ethyltrimonium chloride acrylate/ethalkonium chloride acrylate copolymer; acrylamides copolymer; acrylamide/sodium acrylate copolymer; acrylamide/sodium acryloyldimethyltaurate copolymer; acrylates/acetoacetoxyethyl methacrylate copolymer; acrylates/beheneth-25 methacrylate copolymer; acrylates/$C_{10}$-$C_{30}$ alkyl acrylate crosspolymer; acrylates/ceteth-20 itaconate copolymer; acrylates/ceteth-20 methacrylate copolymer; acrylates/laureth-25 methacrylate copolymer; acrylates/palmeth-25 acrylate copolymer; acrylates/palmeth-25 itaconate copolymer; acrylates/steareth-50 acrylate copolymer; acrylates/steareth-20 itaconate copolymer; acrylates/steareth-20 methacrylate copolymer; acrylates/stearyl methacrylate copolymer; acrylates/vinyl isodecanoate crosspolymer; acrylic acid/acrylonitrogens copolymer; adipic acid/methyl DEA crosspolymer; agar; agarose; *alcaligenes* polysaccharides; algin; alginic acid; almondamide DEA; almondamidopropyl betaine; aluminum/magnesium hydroxide stearate; ammonium acrylates/acrylonitrogens copolymer; ammonium acrylates copolymer; ammonium acryloyldimethyltaurate/vinyl formamide copolymer; ammonium acryloyldimethyltaurate/VP copolymer; ammonium alginate; ammonium chloride; ammonium polyacryloyldimethyl taurate; ammonium sulfate; amylopectin; apricotamide DEA; apricotamidopropyl betaine; arachidyl alcohol; arachidyl glycol; *Arachis hypogaea* (peanut) flour; ascorbyl methylsilanol pectinate; *astragalus* gummifer gum; attapulgite; *Avena sativa* (oat) kernel flour; avocadamidopropyl betaine; azelamide MEA; babassuamide DEA; babassuamide MEA; babassuamidopropyl betaine; behenamide DEA; behenamide MEA; behenamidopropyl betaine; behenyl betaine; bentonite; butoxy chitosan; *caesalpinia spinosa* gum; calcium alginate; calcium carboxymethyl cellulose; calcium carrageenan; calcium chloride; calcium potassium carbomer; calcium starch octenylsuccinate; $C_{20-40}$ alkyl stearate; canolamidopropyl betaine; capramide DEA; capryl/capramidopropyl betaine; carbomer; carboxybutyl chitosan; carboxymethyl cellulose acetate butyrate; carboxymethyl chitin; carboxymethyl chitosan; carboxymethyl dextran; carboxymethyl hydroxyethylcellulose; carboxymethyl hydroxypropyl guar; carnitine; cellulose acetate propionate carboxylate; cellulose gum; *ceratonia siliqua* gum; cetearyl alcohol; cetyl alcohol; cetyl babassuate; cetyl betaine; cetyl glycol; cetyl hydroxyethylcellulose; chimyl alcohol; cholesterol/HDI/pullulan copolymer; cholesteryl hexyl dicarbamate pullulan; citrus aurantium *dulcis* (orange) peel extract; cocamide DEA; cocamide MEA; cocamide MIPA; cocamidoethyl betaine; cocamidopropyl betaine; cocamidopropyl hydroxysultaine; coco-betaine; coco-hydroxysultaine; coconut alcohol; coco/oleamidopropyl betaine; coco-Sultaine; cocoyl sarcosinamide DEA; cornamide/cocamide DEA; cornamide DEA; croscarmellose; crosslinked *bacillus*/glucose/sodium glutamate ferment; *cyamopsis tetragonoloba* (guar) gum; decyl alcohol; decyl betaine; dehydroxanthan gum; dextrin; dibenzylidene sorbitol; diethanolaminooleamide DEA; diglycol/CHDM/is ophthalates/SIP copolymer; dihydroabietyl behenate; dihydrogenated tallow benzylmonium hectorite; dihydroxyaluminum aminoacetate; dimethicone/PEG-10 crosspolymer; dimethicone/PEG-crosspolymer; dimethicone propyl PG-betaine; dimethylacrylamide/acrylic acid/polystyrene ethyl methacrylate copolymer; dimethylacrylamide/s odium acryloyldimethyltaurate crosspolymer; disteareth-100 IPDI; DMAPA acrylates/acrylic acid/acrylonitrogens copolymer; erucamidopropyl hydroxysultaine; ethylene/sodium acrylate copolymer; gelatin; gellan gum; glyceryl alginate; *glycine soja* (soybean) flour; guar hydroxypropyltrimonium chloride; hectorite; hyaluronic acid; hydrated silica; hydrogenated potato starch; hydrogenated tallow; hydrogenated tallowamide DEA; hydrogenated tallow betaine; hydroxybutyl methylcellulose; hydroxyethyl acrylate/sodium acryloyldimethyl taurate copolymer; hydroxyethylcellulose; hydroxyethyl chitosan; hydroxyethyl ethylcellulose; hydroxyethyl stearamide-MIPA; hydroxylauryl/hydroxymyristyl betaine; hydroxypropylcellulose; hydroxypropyl chitosan; hydroxypropyl ethylenediamine carbomer; hydroxypropyl guar; hydroxypropyl methylcellulose; hydroxypropyl methylcellulose stearoxy ether; hydroxypropyl starch; hydroxypropyl starch phosphate; hydroxypropyl xanthan gum; hydroxystearamide MEA; isobutylene/sodium maleate copolymer; isostearamide DEA; isostearamide MEA; isostearamide mIPA; isostearamidopropyl betaine; lactamide MEA; lanolinamide DEA; lauramide DEA; lauramide MEA; lauramide MIPA; lauramide/myristamide DEA; lauramidopropyl betaine; lauramidopropyl hydroxysultaine; laurimino bispropanediol; lauryl alcohol; lauryl betaine; lauryl hydroxysultaine; lauryl/myristyl glycol hydroxypropyl ether; lauryl sultaine; lithium magnesium silicate; lithium magnesium sodium silicate; macrocystis pyrifera (kelp); magnesium alginate; magnesium/aluminum/hydroxide/carbonate; magnesium aluminum silicate; magnesium silicate; magnesium trisilicate; methoxy PEG-22/dodecyl glycol copolymer; methylcellulose; methyl ethylcellulose; methyl hydroxyethylcellulose; microcrystalline cellulose; milkamidopropyl betaine; minkamidopropyl betaine; MIPA-myristate; montmorillonite; Moroccan lava clay; myristamidopropyl betaine; myristamidopropyl hydroxysultaine; myristyl alcohol; myristyl betaine; natto gum; nonoxynyl hydroxyethylcellulose; oatamidopropyl betaine; octacosanyl glycol isostearate; octadecene/MA copolymer; oleamide DEA; oleamidopropyl betaine; oleamidopropyl hydroxysultaine; oleyl betaine; olivamidopropyl betaine; palmamidopropyl betaine; palmitamidopropyl betaine; palm kernel alcohol; palm kernelamidopropyl betaine; pectin; PEG-800; PEG-crosspolymer; PEG-150/decyl alcohol/SMDI copolymer; PEG-175 diisostearate; PEG-190 distearate; PEG-15 glyceryl tristearate; PEG-140 glyceryl tristearate; PEG-240/HDI copolymer bis-decyltetradeceth-20 ether; PEG-100/IPDI copolymer; PEG-180/laureth-50/TMMG copolymer; PEG-10/lauryl dimethicone crosspolymer; PEG-15/lauryl dimethicone crosspolymer; PEG-2M; PEG-5M; PEG-7M; PEG-9M; PEG-14M; PEG-20M; PEG-23M; PEG-25M; PEG-45M; PEG-65M; PEG-90M; PEG-115M; PEG-160M; PEG-180M; PEG-120 methyl glucose trioleate; PEG-180/octoxynol-40/TMMG copolymer; PEG-150 pentaerythrityl tetrastearate; PEG-4 rapeseedamide; PEG-150/stearyl alcohol/SMDI copolymer; *phaseolus angularis* seed powder; polianthes *tuberosa* extract; polyacrylate-3; polyacrylic acid; polycyclopentadiene; polyether-1; polyethylene/isopropyl maleate/MA copolyol; polyglyceryl-3 disiloxane dimethicone; polyglyceryl-3 polydimethylsiloxyethyl dimethicone; polymethacrylic acid; polyquaternium-52; polyvinyl alcohol; potassium alginate; potassium aluminum polyacrylate; potassium carbomer; potassium carrageenan; potassium chloride; potassium palmate; potassium polyacrylate; potassium sulfate; potato starch modified; PPG-2 cocamide; PPG-1 hydroxyethyl caprylamide; PPG-2 hydroxyethyl cocamide; PPG-2 hydroxycthyl coco/isostcaramide; PPG-3 hydroxycthyl soyamide; PPG-14 laureth-60 hexyl dicarbamate; PPG-14 laureth-60 isophoryl dicarbamate; PPG-14 palmeth-60 hexyl dicarbamate; propylene glycol alginate; PVP/decene copolymer; PVP montmorillonite; *pyrus cydonia* seed; *pyrus malus* (apple) fiber; rhizobian gum; ricebranamide DEA; ricinoleamide DEA; ricinoleamide MEA; ricinoleamide MIPA; ricinoleamidopropyl betaine; ricinoleic acid/adipic acid/AEEA copolymer; *rosa multiflora* flower wax; *sclerotium* gum; sesamide DEA; sesamidopropyl betaine; sodium acrylate/acryloyldimethyl taurate copolymer; sodium acrylates/acrolein copolymer; sodium acrylates/acrylonitrogens copolymer; sodium acrylates copolymer; sodium acrylates crosspolymer; sodium acrylate/sodium acrylamidomethylpropane sulfonate copolymer; sodium acrylates/vinyl isodecanoate crosspolymer; sodium acrylate/vinyl alcohol copolymer; sodium carbomer; sodium carboxymethyl chitin; sodium carboxymethyl dextran; sodium carboxymethyl beta-glucan; sodium carboxymethyl starch; sodium carrageenan; sodium cellulose sulfate; sodium chloride; sodium cyclodextrin sulfate; sodium hydroxypropyl starch phosphate; sodium isooctylene/MA copolymer; sodium magnesium fluorosilicate; sodium oleate; sodium palmitate; sodium palm kernelate; sodium polyacrylate; sodium polyacrylate starch; sodium polyacryloyldimethyl taurate; sodium polygamma-glutamate; sodium polymethacrylate; sodium polystyrene sulfonate; sodium silicoaluminate; sodium starch octenylsuccinate; sodium stearate; sodium stearoxy PG-hydroxyethylcellulose sulfonate; sodium styrene/acrylates copolymer; sodium sulfate; sodium tallowate; sodium tauride acrylates/acrylic acid/acrylonitrogens copolymer; sodium tocopheryl phosphate; *Solanum tuberosum* (potato) starch; soyamide DEA; soyamidopropyl betaine; starch/acrylates/acrylamide copolymer; starch hydroxypropyltrimonium chloride; stearamide AMP; stearamide DEA; stearamide DEA-distearate; stearamide DIBA-stearate; stearamide MEA; stearamide MEA-stearate; stearamide MIPA; stearamidopropyl betaine; steareth-60 cetyl ether; steareth-100/PEG-136/HDI copolymer; stearyl alcohol; stearyl betaine; sterculia *urens* gum; synthetic fluorphlogopite; tallamide DEA; tallow alcohol; tallowamide DEA; tallowamide MEA; tallowamidopropyl betaine; tallowamidopropyl hydroxysultaine; tallowamine oxide; tallow betaine; tallow dihydroxyethyl betaine; tamarindus indica seed gum; tapioca starch; TEA-alginate; TEA-carbomer; TEA-hydrochloride; trideceth-2 carboxamide MEA; tridecyl alcohol; triethylene glycol dibenzoate; trimethyl pentanol hydroxyethyl ether; *Triticum vulgare* (wheat) germ powder; *Triticum vulgare* (wheat) kernel flour; *Triticum vulgare* (wheat) starch; tromethamine acrylates/acrylonitrogens copolymer; tromethamine magnesium aluminum silicate; undccyl alcohol; undccylcnamidc DEA; undccylcnamidc MEA; undecylenamidopropyl betaine; welan gum; wheat germamide DEA; wheat germamidopropyl betaine; xanthan gum; yeast beta-glucan; yeast polysaccharides and *Zea mays* (corn) starch. In other embodiment, the thickeners or viscosity increasing agents include carbomer, aculyn and Stabileze®, e.g. crosslinked acrylic acid, crosslinked poly(methylvinyl ether/maleic anhydride) copolymer, acrylamides, carboxymethyl cellulose and any combinations thereof. In one embodiment of the present disclosure, the additional thickening or viscosity increasing agents can include, but are not limited to, carbomer, cetyl hydroxyethyl cellulose, crosslinked polyvinylpyrrolidone, sodium polyacrylate, xanthan gum or any combinations thereof.

The sunscreen composition of the present disclosure can further comprise one or more buffers. Suitable examples of buffers can include, but are not limited to, alkali or alkali earth carbonates, phosphates, bicarbonates, citrates, borates, acetates, acid anhydrides, succinates and any combinations thereof.

In still another aspect, the present disclosure provides a sunscreen composition comprising: (i) 0.01 wt. % to 20 wt. % of vinyl pyrrolidone (VP)/styrene copolymer; (ii) 0.01 wt. % to 50 wt. % of at least one sunscreen active ingredient selected from the group consisting of butyl methoxydibenzoylmethane, octyl salicylate, octocrylene, benzophenone-3 and homosalate; and (iii) 0.01 wt. % to 50 wt. % of at least one pharmaceutically or cosmetically or dermatologically acceptable excipient, and wherein, the sunscreen composition can further optionally comprise a vinyl pyrrolidone/eicosene copolymer as a second copolymer in addition to above said vinyl pyrrolidone (VP)/styrene copolymer of the composition, wherein the use ranges of these combined copolymers is also in the range of 0.01 wt. % to 20 wt. % based on total composition weight.

The sunscreen composition of the present disclosure can be used for a variety of cosmetic or dermatologic uses, especially for protection of human and/or animal skin from damages caused by ultra-violet (UV) radiations from the sun rays. The sunscreen composition according to the present disclosure can be made into a wide variety of delivery forms. These forms can include, but are not limited to, emulsions, solutions, gels, or fusions. Suitable examples of such forms can include, but are not limited to, an oil-in-water emulsion, a water-in-oil emulsion, an oil-water-oil emulsion, a water-oil-water emulsion, a water-in-silicone emulsion, an oily solution, a lipid fusion, a hydro-alcoholic gel, an anhydrous gel, an aqueous gel, an alcoholic solutions or a hydro-alcoholic solution. In one non-limiting embodiment of the present disclosure, the sunscreen composition can be in the form of an oil-in-water emulsion. Further, suitable product form of the sunscreen composition of the present disclosure can include, but are not limited to, lotions, creams, gels, sticks, sprays, ointments, mousses, and compacts/powders.

The sunscreen composition according to the present disclosure can be employed in various end-uses products, such as recreation or daily-use sunscreens, moisturizers, cosmetics/make-up, cleansers/toners, anti-aging products, or combinations thereof.

In another aspect, the present disclosure provides a method of protecting human skin and/or animal skin against damages caused by ultra-violet (UV) radiations from the sunrays. The method comprises applying the sunscreen composition of present application to human skin and/or animal akin. The sunscreen composition of the present disclosure cannot be limited to those used primarily as sunscreens. The sunscreen compositions can also be useful in other topically applied compositions wherein the sunscreen active is a secondary ingredient in the formulation. Such formulations include lipsticks, make-up, lip balm, eyeshadow, hair dyes and conditioners or any application where sun protection may be deemed beneficial.

The sunscreen compositions of the present disclosure may be prepared using methods that are well known to an artisan of ordinary skill in the field of cosmetics formulation. In general, the method of preparing the sunscreen composition of the present disclosure can comprise the steps of: mixing various ingredients under continuous stirring, if necessary under heat, to obtain a uniform and homogenous composition. The sunscreen composition of the present disclosure can be packed in any package or container suitable for a sunscreen composition.

In still another aspect, the present disclosure provides a use of a sunscreen composition for protecting human skin and/or animal skin against damages caused by ultra-violet (UV) radiations from the sun, wherein the composition comprising: (i) 0.01 wt. % to 20 wt. % of (a) a first copolymer of vinyl pyrrolidone (VP) and styrene, and (b) optionally a second copolymer of vinyl pyrrolidone and at least one $C_2$ to $C_{40}$ alkene; (ii) 0.01 wt. % to 50 wt. % of at least one sunscreen active ingredient(s); and (iii) 0.01 wt. % to 50 wt. % of at least one pharmaceutically or cosmetically or dermatologically acceptable excipient. The $C_2$ to $C_{40}$ alkene can include $C_2$ to $C_{40}$ aliphatic alkene or $C_2$ to $C_{40}$ aromatic alkene (aryl substitute alkene) or any combinations thereof. Further, the $C_2$ to $C_{40}$ aliphatic alkene can be a linear alkene or a branched chain alkene. Examples of such alkenes can include, but are not limited to, pentadecene, hexadecene, heptadecene, octadecene, nonadecene, eicosene, docosene and triacontene.

In one non-limiting embodiment of the present disclosure, the second copolymer can include (i) a vinyl pyrrolidone (VP)/eicosene copolymer or (ii) a vinyl pyrrolidone (VP)/hexadecene copolymer or (iii) a vinyl pyrrolidone (VP)/tricontanyl copolymer or any combinations thereof. In another non-limiting embodiment of the present disclosure, the sunscreen composition comprises a mixture of (a) vinyl pyrrolidone (VP)/styrene copolymer as the first copolymer and (ii) vinyl pyrrolidone (VP)/eicosene copolymer as the second copolymer. Further, the vinyl pyrrolidone (VP)/styrene copolymer and vinyl pyrrolidone (VP)/eicosene copolymer can be mixed in a weight ratio of from 2 to 10:1 to 4.

The pH of the sunscreen composition of the present disclosure can vary in the range of from about 4 to about 8 or in the range of from about 5 to about 7. Further, the sunscreen composition of the present disclosure can have a Sun Protection Factor (SPF) value of at least 40. In one non-limiting embodiment of the present disclosure, the SPF value can vary in the range of from about 40 to about 70 or from about 50 to 66. The inventors of the present disclosure have surprisingly found out that the presence of vinyl pyrrolidone (VP)/styrene copolymer as the first copolymer boosts the SPF value of the sunscreen active ingredients present in the sunscreen composition of the present disclosure. The SPF value of the sunscreen active ingredients can be further enhanced by using a combination of the first copolymer and at least one of the second copolymers, as hereinabove described in the present disclosure. The sunscreen composition according to the present disclosure can exhibit a percent increase in SPF value of at least 50%, more particularly at least 60%, and in accordance with certain embodiments at least 70% as compared to control compositions that do not comprise the first copolymer, either alone or in combination with the second copolymer of the present disclosure. Further, the sunscreen composition of the present disclosure can be advantageous even when exhibiting SPF boosts as low as 5%, 10%, 20%, 25%, 30% or 40%. SPF boost values can be determined using the calculations set forth in the Food and Drug Administration (FDA) proposed amendments of the Final Monograph on Sunscreen Products for Over-the-Counter Human Use as published in the Federal Register on Aug. 27, 2007 at Volume 72, Number 165, pages 49070-49122, the contents of which are hereby incorporated by reference.

Further, the sunscreen composition of the present disclosure can also exhibit an enhanced water resistance of at least 50%, as compared to the compositions (control composition) that do not comprise the first copolymer, either alone or in combination with the second polymer. In another embodiment of the present disclosure, the sunscreen composition can also exhibit an enhanced water resistance of at least 60% or of at least 70% or at least 80% as compared to the control composition.

These examples are presented herein for purposes of illustration of the present disclosure and are not intended to be limiting, for example, the method of treating textile materials.

EXAMPLES

Example 1 (Ex.1): Sunscreen Composition (Non-Ionic Emulsion) Comprising 7.5 wt. % of Vinyl Pyrrolidone (VP)/Styrene Copolymer This example describes a process for preparing sunscreen composition in non-ionic emulsion form comprising only vinyl pyrrolidone (VP)/styrene copolymer (7.5 wt. % based on total sunscreen composition weight). The sunscreen composition of this examples was prepared by using ingredients of Phase A, Phase B, Phase C and Phase D and in amounts listed in Table 1 below. In a primary one-liter beaker, water and propylene glycol were mixed together in amounts listed in Table-1 and heated to 75° C.-80° C. Carbomer was then sprinkled into the beaker and the mixing was continued until a smooth mixture was obtained. Afterwards, paraben (Liquapar MEP) was added to obtain Phase A. Phase B was prepared in a separate beaker. For this, Phase B ingredients, in amounts listed in Table 1, were mixed together and heated to 75° C.-80° C. The Phase B was then added to Phase A. The mixing of Phase A and Phase B was carried out until a homogenized mixture thereof was obtained. The homogenized mixture of Phase A and Phase B was then cooled to 60-65° C., and Phase C was added to it. The mixing of Phase A, Phase B and Phase C was carried out until a homogenized mixture thereof was obtained. pH of the homogenized mixture was checked and adjusted as needed. The mixing was continued until the homogenized mixture of Phase A, Phase B and Phase C was cooled to less than 50° C. and then Phase D was added in an amount listed in Table 1. The resultant mixture of Phase A, Phase B, Phase C and Phase D thus obtained was changed to sweep mixing and the mixing was continued until the mixture was cooled to 30° C. The sunscreen compositions thus obtained (non-ionic emulsion form) was analyzed for pH, viscosity and Sun Protection factor value. pH of the non-ionic emulsion was 5.74 and viscosity of 44,600 cps. The sunscreen composition (non-ionic emulsion) of this example was tested for both, in-vivo and in-vitro SPF value, and for water resistance value. The in-vitro and in-vitro SPF values are 55 and 51, respectively; and 80 min. water resistance is 52.61.

Comparative Example 1 (Comp. Ex.1)

Figure 2:
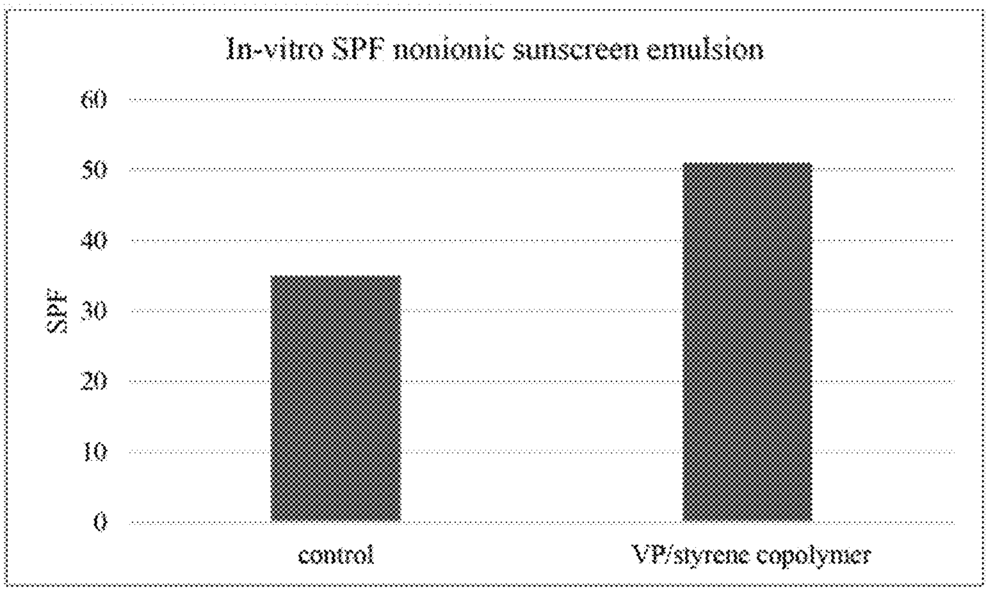
FIG. 2 shows "in-vitro" SPF testing results of sunscreen composition (non-ionic emulsion) comprising VP/styrene copolymer.

Another experiment was carried out in the same manner as described above for example 1 for preparing a sunscreen composition without VP/styrene copolymer (Control composition). The composition of this example was prepared by using ingredients and in amounts listed in Table 1 below. The composition of this example was analyzed for its SPF value (both in-vivo and in-vitro) and water resistance analysis similar to the composition of example 1. The in-vivo and in-vitro SPF values are 33.49 and 35, respectively, and 80 min. water resistance is 21.06. The SPF (in-vivo) and water resistance values of the compositions of example 1 and comparative example 1 were shown in FIG. 1 Similarly, in-vitro SPF values of the sunscreen compositions of example 1 and comparative example 1 were shown in FIG. 2. It is clearly evident (from the provided FIG. 1 and FIG. 2) that the sunscreen composition of example 1 comprising 7.5 wt. % of VP/styrene copolymer showed SPF boosting over control composition (without VP/styrene copolymer). Further the presence of VP/styrene copolymer also showed enhanced water resistance as compared to the control composition (without VP/styrene copolymer).

TABLE 1

Sunscreen compositions (non-ionic emulsions): Example 1 and Comparative example 1

| Phase | Ingredients (INCI) | % W/W Com.Ex.1 | % W/W Ex.1 |
|---|---|---|---|
| A | Water | 60.2 | 52.7 |
| | Propylene glycol | 2.0 | 2.0 |
| | Carbomer | 0.3 | 0.3 |
| | Liquapar MEP (Phenoxyethanol (and) Methylparaben (and) Ethylparaben (and) Propylparaben} | 1.0 | 1.0 |
| B | Avobenzonc | 3.0 | 3.0 |
| | Ethylhexyl Salicylate | 5.0 | 5.0 |
| | Octocrylene | 2.8 | 2.8 |
| | Benzophenone-3 | 6.0 | 6.0 |
| | Homosalate | 10.0 | 10.0 |
| | PEG-100 Stearate (and) Glyceryl Stearate | 4.0 | 4.0 |
| | Cetyl Lactate | 5.0 | 5.0 |
| C | Sodium hydroxide 10% | 0.7 | 0.7 |
| D | VP/styrene Copolymer (Polectron™ 430) | Nil | 7.5 |
| | Total | 100 | 100 |

Example 2 (Ex.2a. Ex.2b and Ex.2c): Sunscreen Compositions (Anionic Emulsions)

This example describes a process for preparing a sunscreen composition in anionic emulsion form. different sunscreen compositions were prepared in this example (compositions corresponding to Ex.2a and Ex.2b in Table 2). All the two sunscreen compositions were prepared using ingredients, in amounts, listed in Table 2 below, and in accordance with the procedure as described above in example 1. All the two compositions differ with respect to the type of copolymers used and its amount. The composition Ex.2a comprises only 2.5 wt. % of VP/styrene copolymer and without VP/eicosene copolymer whereas the composition Ex.2b comprises a combination of VP/styrene copolymer (2.5 wt. %) and VP/eicosene copolymer (1.0 wt. %).

Comparative Example 2 (Comp. Ex.2a and Comp.Ex.2b)

Another experiment was carried out in the same manner as described above for example 1 for preparing two different sunscreen compositions (control compositions in anionic emulsion forms): First control composition (Comp. Ex.2a) is without VP/styrene and VP/eicosene copolymers, whereas the second control composition (Comp.Ex.2b) comprises only 1.0 wt. % of VP/eicosene copolymer. The control compositions of this example were prepared by using ingredients and in amounts listed in Table 2 below.

TABLE 2

Sunscreen compositions (anionic emulsion forms): example 2 and comparative example 2

| Phase | Ingredients (INCI) | % W/W Comp. Ex.2a163 | % W/W Comp. Ex.2b | % W/W Ex. 2a | % W/W Ex. 2b |
|---|---|---|---|---|---|
| A | Water | 49.1 | 48.1 | 46.6 | 45.6 |
| | Glycerin | 5.0 | 5.0 | 5.0 | 5.0 |
| | Propylene glycol | 5.0 | 5.0 | 5.0 | 5.0 |
| | Disodium EDTA | 0.1 | 0.1 | 0.1 | 0.1 |
| | Phenoxyethanol (and) Caprylyl Glycol | 1.0 | 1.0 | 1.0 | 1.0 |
| | Sodium hydroxide 10% | 0.3 | 0.3 | 0.3 | 0.3 |
| B | Acrylic Acid/VP Crosspolymer | 0.5 | 0.5 | 0.5 | 0.5 |
| C | Avobenzone | 3.0 | 3.0 | 3.0 | 3.0 |
| | Benzophenone-3 | 6.0 | 6.0 | 6.0 | 6.0 |
| | Ethylhexyl Salicylate | 5.0 | 5.0 | 5.0 | 5.0 |
| | Octocrylene | 5.0 | 5.0 | 5.0 | 5.0 |
| | Homosalate | 10.0 | 10.0 | 10.0 | 10.0 |
| | Diisopropyl Adipate | 4.0 | 4.0 | 4.0 | 4.0 |
| | Crodafos CES (Cetearyl Alcohol, Dicetyl Phosphate and Ceteth-10 Phosphate) | 5.0 | 5.0 | 5.0 | 5.0 |
| | VP/Eicosene Copolymer | Nil | 1.0 | Nil | 1.0 |
| D | Sodium hydroxide 10% | 1.0 | 1.0 | 1.0 | 1.0 |
| | VP/styrene copolymer | Nil | Nil | 2.5 | 2.5 |
| | Total | 100 | 100 | 100 | 100 |

Figure 3:
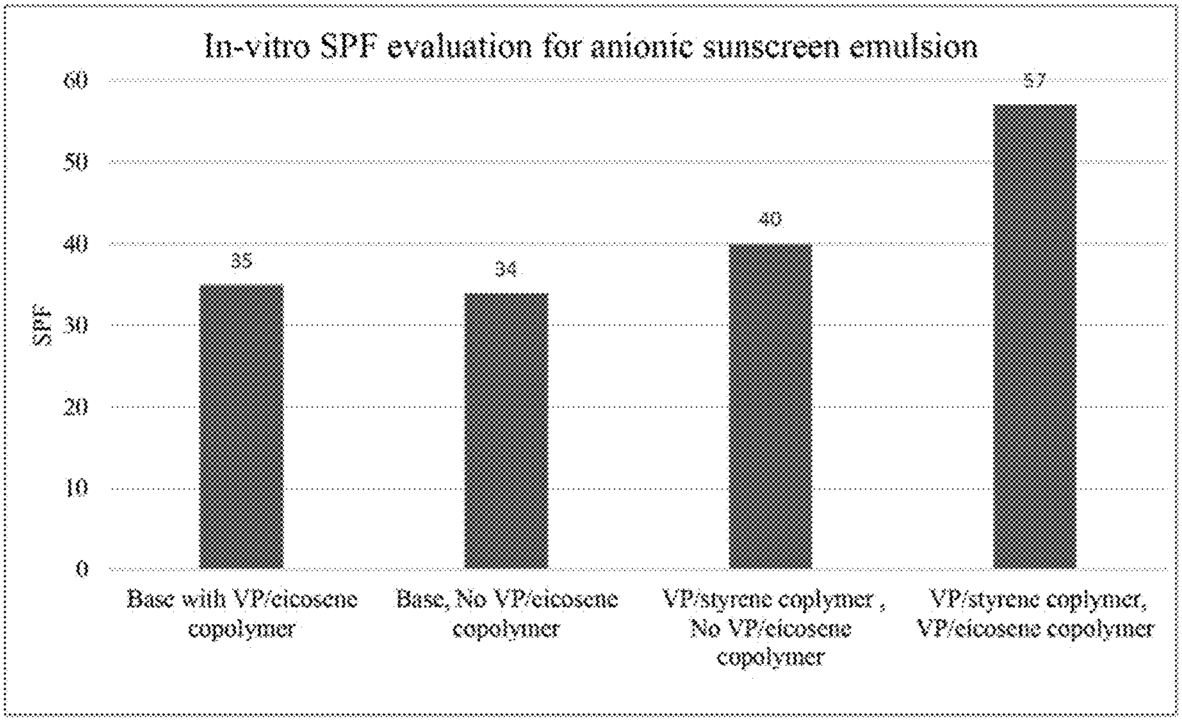
FIG. 3 shows "in-vitro" SPF testing results of sunscreen composition (non-ionic) comprising a combination of VP/styrene copolymer and VP/eicosene copolymer.
Figure 4:
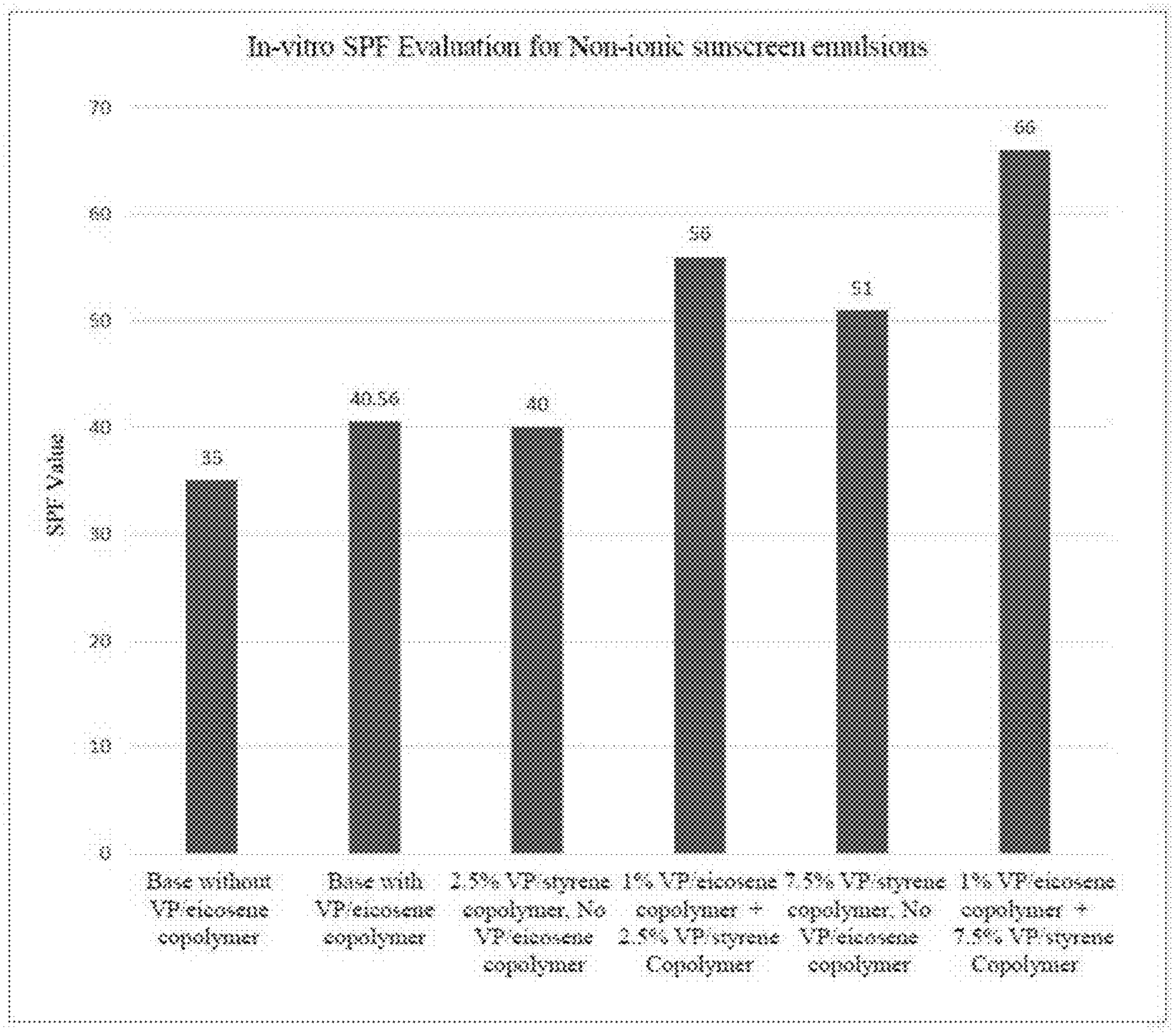
FIG. 4 shows "in-vitro" SPF testing results of the sunscreen composition (anionic) comprising a combination of VP/styrene copolymer and VP/eicosene copolymer.

All the compositions of example 2 were analyzed for their SPF values (in-vitro). The in-vitro SPF values were shown in FIG. 3. It is clearly evident from the provided FIG. 3 that the sunscreen composition comprising only 1.0 wt. % VP/eicosene copolymer (Comp.Ex.2b) showed marginal increase its SPF value (35) as compared to the control composition Comp.Ex.2a (SPF value 34). Similarly, the sunscreen composition comprising only 2.5 wt. % VP/styrene copolymer (Ex.2a) showed SPF boosting (SPF value 40) over control composition Comp.Ex.2a (SPF value 34). The sunscreen composition (Ex.2b) comprising a combination VP/styrene (2.5 wt. %) and VP/eicosene (1.0 wt. %) copolymers showed better SPF boosting (SPF value 57) over the control compositions Comp.Ex.2a and Comp.Ex.2b.

Example 3 (Ex.3):—Sunscreen Composition (Nonionic Emulsion Form) with 1.0 wt. % VP/Eicosene Copolymer This example describes a process for preparing a sunscreen composition (nonionic emulsion form) comprising 1.0 wt. % of VP/eicosene copolymer. Phase A, Phase B and Phase C were prepared using the ingredients and in amounts listed in Table 3 below. In a primary one-liter beaker, water and propylene glycol was mixed together in amounts listed in table 3 at 75° C. to 80° C. temperature. Carbomer was then sprinkled into the beaker and the mixing was continued until a smooth mixture was obtained. Afterwards, paraben was added to obtain Phase A. Phase B was prepared in a separate beaker. For this, Phase B ingredients, in amounts listed in Table 3, were mixed together and heated to 75° C.-80° C. The Phase B was then added to Phase A. The mixing of Phase A and Phase B was carried out until a homogenized mixture thereof was obtained. The homogenized mixture of Phase A and Phase B was then cooled to 60-65° C., and Phase C was added to it. The mixing of Phase A, Phase B and Phase C was carried out until a homogenized mixture thereof (non-ionic emulsion) was obtained. The mixing was continued until the emulsion cooled to 30° C.

The sunscreen composition of this example has a pH of 5.95, a viscosity of 73800 cps, and a SPF value of 40.56.

TABLE 3

| Sunscreen composition (nonionic emulsion): 1.0 wt. % of VP/eicosene copolymer | | |
|---|---|---|
| Phase | Ingredients (INCI) | % W/W Ex.3 |
| A | Water | 62.2 |
| | Propylene glycol | 2.0 |
| | Carbomer | 0.3 |
| | Phenoxyethanol (and) Methylparaben (and) Ethylparaben (and) Propylparaben | 1.0 |
| B | Avobenzone | 3.0 |
| | Ethylhexyl Salicylate | 5.0 |
| | Octocrylene | 2.8 |
| | Benzophenone-3 | 6.0 |
| | Homosalate | 10.0 |
| | PEG-100 Stearate (and) Glyceryl Stearate | 4.0 |
| | VP/cicosene Copolymer | 1.0 |
| | Diisopropyl Adipate | 2.0 |
| C | Sodium hydroxide 10% | 0.7 |
| | Total | 100 |

Example 4 (Ex.4): Sunscreen Composition (Non-Ionic Emulsion Form): 2.5 wt. % VP/Styrene Copolymer (without VP/Eicosene Copolymer)

This example describes a process for preparing a sunscreen composition (nonionic emulsion from) comprising 2.5 wt. % of VP/styrene copolymer. The sunscreen composition of this example was prepared using the ingredients in amounts listed in Table 4 below, and in the manner as described above in example 3. The sunscreen composition of this example has a pH of 6.0, a viscosity of 61800 cps, and a SPF value of 40.

TABLE 4

| Sunscreen composition (nonionic emulsion form): 2.5 wt. % VP/styrene copolymer | | |
|---|---|---|
| Phase | Ingredients (INCI) | % W/W Ex.4 |
| A | Water | 60.7 |
| | Propylene glycol | 2.0 |
| | Carbomer | 0.3 |
| | Phenoxyethanol (and) Methylparaben (and) Ethylparaben (and) Propylparaben | 1.0 |
| B | Avobenzone | 3.0 |
| | Ethylhexyl Salicylate | 5.0 |
| | Octocrylene | 2.8 |
| | Benzophenonc-3 | 6.0 |
| | Homosalate | 10.0 |
| | PEG-100 Stearate (and) Glyceryl Stearate | 4.0 |
| | Diisopropyl adipate | 2.0 |
| | VP/eicosene copolymer | Nil |
| C | Sodium hydroxide 10% | 0.7 |
| | VP/styrene copolymer | 2.5 |
| | Total | 100 |

Example 5 (Ex.5): Sunscreen Composition (Nonionic Emulsion Form): 2.5 wt. % of VP/Styrene Copolymer and 1.0 wt. % of VP/Eicosene Copolymer This example describes a process for preparing a sunscreen composition comprising 2.5 wt. % of VP/styrene copolymer and 1.0 wt. % of VP/eicosene copolymer. The sunscreen composition of this example was prepared using the ingredients and in amount listed in Table 5 below, and in the manner as described above in example 3. The sunscreen composition (nonionic emulsion form) of this example has a pH of 5.95, a viscosity of 75800 cps, and a SPF value of 56.

TABLE 5

| Sunscreen composition (nonionic emulsion form): 2.5 wt. % of VP/styrene copolymer and 1.0 wt. % of VP/eicosene copolymer. | | |
|---|---|---|
| Phase | Ingredients (INCI) | % W/W 12695-165 |
| A | Water | 59.7 |
| | Propylene glycol | 2.0 |
| | Carbomer | 0.3 |
| | Phenoxyethanol (and) Methylparaben (and) Ethylparaben (and) Propylparaben | 1.0 |
| B | Avobenzone | 3.0 |
| | Ethylhexyl Salicylate | 5.0 |
| | Octocrylene | 2.8 |
| | Benzophenone-3 | 6.0 |
| | Homosalate | 10.0 |
| | PEG-100 Stearate (and) Glyceryl Stearate | 4.0 |
| | Diisopropyl adipate | 2.0 |
| | VP/cicosene copolymer | 1.0 |
| C | Sodium hydroxide 10% | 0.7 |
| | VP/styrene copolymer | 2.5 |
| | Total | 100 |

Example 6: Sunscreen Composition (Nonionic Emulsion Form): 7.5 wt. % of VP/Styrene Copolymer (without VP/Eicosene Copolymer)

The example describes a process for preparing a sunscreen composition (nonionic emulsion form) comprising 7.5 wt. % of VP/styrene copolymer. The sunscreen composition of this example was prepared using the ingredients and in amounts listed in Table 6 below, and in accordance with the procedure described above in example 3. The sunscreen composition of this example has a pH of 5.95, a viscosity of 44600 cps, and a SPF value of 51.

TABLE 6

Sunscreen composition (nonionic emulsion): 7.5 wt. % of VP/styrene copolymer

| Phase | Ingredients (INCI) | % W/W Ex.6 |
|---|---|---|
| A | Water | 55.7 |
| | Propylene glycol | 2.0 |
| | Carbomer | 0.3 |
| | Phenoxyethanol (and) Methylparaben (and) Ethylparaben (and) Propylparaben | 1.0 |
| | Avobenzone | 3.0 |
| | Ethylhexyl Salicylate | 5.0 |
| | Octocrylene | 2.8 |
| R | Benzophenone-3 | 6.0 |
| | Homosalate | 10.0 |
| | PEG-100 Stearate (and) Glyceryl Stearate | 4.0 |
| | Diisopropyl adipate | 2.0 |
| | VP/Eicosene copolymer | Nil |
| C | Sodium hydroxide 10% | 0.7 |
| | VP/styrene copolymer | 7.5 |
| | Total | 100 |

Example 7 (Ex.7): Sunscreen Composition (Nonionic Emulsion Form): VP/Styrene Copolymer (7.5 wt. %) and VP/Eicosene Copolymer (1.0 wt. %)

This example describes a process for preparing a sunscreen composition comprising a mixture of 7.5 wt. % VP/styrene and 1.0 wt. % of VP/eicosene copolymer. The sunscreen composition of this example was prepared using the ingredients of Phase A, Phase B and Phase C and in amount listed in Table 7 below. Further, the sunscreen composition of this example was prepared in accordance with the procedure described above in example 3. The sunscreen composition of this example has a pH=5.62, a viscosity of 53600 cps, and a SPF value of 66.

TABLE 7

Sunscreen composition (nonionic emulsion): VP/styrene (7.5 wt. %) and (1.0 wt. %)

| Phase | Ingredients (INCI) | % W/W Ex.7 |
|---|---|---|
| A | Water | 54.7 |
| | Propylene glycol | 2.0 |
| | Carbomer | 0.3 |
| | Phenoxyethanol (and) Methylparaben (and) Ethylparaben (and) Propylparaben | 1.0 |
| B | Avobenzone | 3.0 |
| | Ethylhexyl Salicylate | 5.0 |
| | Octocrylene | 2.8 |
| | Benzophenone-3 | 6.0 |
| | Homosalate | 10.0 |
| | PEG-100 Stearate (and) Glyceryl Stearate | 4.0 |
| | VP/Eicosene copolymer | 1.0 |
| | Diisopropyl adipate | 2.0 |
| C | Sodium hydroxide 10% | 0.7 |
| | VP/styrene copolymer | 7.5 |
| | Total | 100 |

Comparative Example 3 (Comp.Ex.3): Preparation of Sunscreen Composition (Nonionic Emulsion Form) without any VP/Styrene and/or VP/Eicosene Copolymer Another experiment was carried out in the same manner as described above for example 3 for preparing a sunscreen composition in nonionic emulsion form without VP/styrene and VP/eicosene copolymers (Control composition). The control composition of this example was prepared using the ingredients and in amounts listed in Table 8 below. The control composition of this example has a pH of 6.04, a viscosity of 73800 cps, and a SPF value of 35.

TABLE 8

Sunscreen composition (nonionic emulsion from) without VP/styrene and VP/eicosene copolymers.

| Phase | Ingredients (INCI) | % W/W Comp. Ex.3 |
|---|---|---|
| A | Water | 63.2 |
| | Propylene glycol | 2.0 |
| | Carbomer | 0.3 |
| | Phenoxyethanol (and) Methylparaben (and) Ethylparaben (and) Propylparaben | 1.0 |
| | Avobenzone | 3.0 |
| | Ethylhexyl Salicylate | 5.0 |
| B | Octocrylene | 2.8 |
| | Benzophenone-3 | 6.0 |
| | Homosalate | 10.0 |
| | PEG-100 Stearate (and) Glyceryl Stearate | 4.0 |
| | Diisopropyl Adipate | 2.0 |
| C | Sodium hydroxide 10% | 0.7 |
| | Total | 100 |

All of the compositions and/or methods disclosed herein can be made and executed without undue experimentation in light of the present disclosure. While the compositions and methods of the present disclosure have been described in terms of preferred embodiments, it will be apparent to those of ordinary skill in the art that variations may be applied to the compositions and/or methods and in the steps or in the sequence of steps of the method described herein without departing from the concept, spirit and scope of the present disclosure. All such similar substitutes and modifications apparent to those skilled in the art are deemed to be within the spirit, scope and concept of the present disclosure.

What is claimed is:

1. A sunscreen composition comprising:

(i) a mixture of vinyl pyrrolidone/styrene copolymer as a first copolymer and vinyl pyrrolidone/eicosene copolymer as a second copolymer;

(ii) 0.01 wt. % to 50 wt. % of at least one sunscreen active ingredient selected from the group consisting of butyl methoxydibenzoylmethane, octyl salicylate, octocrylene, benzophenone-3, and homosalate; and (iii) 0.01 wt. % to 50 wt. % of at least one pharmaceutically or cosmetically or dermatologically acceptable excipient, wherein the mixture of first copolymer and second copolymer is present in an amount of from about 0.1 wt. % to about 10.0 wt. % of the total composition weight, wherein the vinylpyrrolidone/styrene and vinyl pyrrolidone/eicosene copolymers are present in a weight ratio of from 2 to 10:1 to 4, wherein the sunscreen composition is in the form of an oil-in-water emulsion, and wherein the sunscreen composition has a pH in the range of from about 4 to about 8.

2. The sunscreen composition according to claim 1, wherein the at least one sunscreen active ingredient is present in the range of from about 0.1 wt. % to about 10.0 wt. % of the total composition weight.

3. The sunscreen composition according to claim 1, wherein the at least one pharmaceutically or cosmetically or dermatologically acceptable excipient is selected from the group consisting of a skin-feel additive, a moisturizing agent, a film forming agent, a waterproofing agent, a pH adjuster, a buffering agent, a chelating agent, an anti-aging agent, an exfoliating agent, a fragrance, an emulsifier, a surfactant, a rheology modifier, a preservative, an emollient, a wax, a conditioner, a lubricant, an anti-oxidant, a diluent, a co-solvent, a humectant, and any combination thereof.

4. The sunscreen composition according to claim 1, wherein the at least one pharmaceutically or cosmetically or dermatologically acceptable excipient is an emulsifier selected from the group consisting of glycol distearate, sorbitan trioleate, glycol stearate, sorbitan sesquioleate, glyceryl stearate, glyceryl dilaurate, lecithin, sorbitan oleate, sorbitan stearate, sorbitan isostearate, oleth-2 and steareth-2, calcium stearoyl lactylate, glyceryl laurate, ceteth-2, PEG-30 dipolyhydroxystearate, glyceryl stearate SE, PEG-4 dilaurate, sorbitan stearates, sucrose cocoate, methyl glucose sesquistearate, sucrose stearate, PEG-10 sunflower glycerides, sodium stearoyl lactylate, sorbitan laurate, PEG-40 sorbitan peroleate, lecithin, laureth-4, PEG-7 glyceryl cocoate, PEG-20 almond glycerides, linoleamide DEA, PEG-25 hydrogenated castor oil, cetearyl glucoside, polysorbate 85, glyceryl stearate (and) PEG-100 stearate, stearamide MEA, oleth-10/polyoxyl 10 oleyl ether NF, oleth-10, oleth-20, ceteth-10, PEG-8 laurate, cocamide MEA, polysorbate 60, PEG-60 almond glycerides, isosteareth-20, lauramide DEA, PEG-30 dipolyhydroxystearate, polysorbate 80, PEG-20 methyl glucose sesquistearate, ceteareth-20, oleth-20, steareth-21, ceteth-20, isoceteth-20, polysorbate 20, laureth-23, PEG-100 stearate, PEG-80 sorbitan laurate, potassium cetyl phosphate, cetearyl alcohol, diacetyl phosphate, ceteth-10 phosphate, and any combination thereof.

5. The sunscreen composition according to claim 3, wherein the at least one pharmaceutically or cosmetically or dermatologically acceptable excipient is a co-solvent selected from the group consisting of one or more polyols, esters, ethers, propoxylated esters, propoxylated alcohols, alkoxylated alcohols, and any combination thereof.

6. The sunscreen composition according to claim 3, wherein the at least one pharmaceutically or cosmetically or dermatologically acceptable excipient is a preservative selected from the group consisting of (i) lower alkyl esters of para-hydroxybenzoates selected from methylparaben, propylparaben, and isobutylparaben; (ii) benzyl alcohol, (iii) phenoxyethanol, (iv) benzoic acid, and combination thereof.

7. The sunscreen composition according to claim 1, wherein the at least one pharmaceutically or cosmetically or dermatologically acceptable excipient is present in an amount of from about 0.01 wt. % to about 20.0 wt. % of the total composition weight.

8. A method of protecting human skin and animal skin against damages caused by ultra-violet radiation, comprising applying the sunscreen composition of claim 1 to the human skin and animal skin.

* * * * *